United States Patent [19]

Ao et al.

[11] Patent Number: 4,678,785

[45] Date of Patent: Jul. 7, 1987

[54] THIADIAZINE COMPOUNDS

[75] Inventors: Hideki Ao; Minoru Obata, both of Oita; Jun Inui, Saitama, all of Japan

[73] Assignee: Yoshitomi Pharmaceutical Industries, Ltd., Osaka, Japan

[21] Appl. No.: 792,402

[22] Filed: Oct. 29, 1985

[30] Foreign Application Priority Data

Oct. 29, 1984 [JP] Japan .................. 59-227300

[51] Int. Cl.[4] .................. C07D 417/04; A61K 31/54
[52] U.S. Cl. .................. 514/222; 544/8
[58] Field of Search .................. 544/8; 514/222

[56] References Cited

U.S. PATENT DOCUMENTS

| | | | |
|---|---|---|---|
| 4,423,045 | 12/1983 | Brown et al. | 544/8 |
| 4,489,073 | 12/1984 | Hargreaves et al. | 544/8 |
| 4,503,054 | 8/1983 | Brown et al. | 544/182 |
| 4,587,246 | 11/1984 | Brown et al. | 544/8 |

FOREIGN PATENT DOCUMENTS 0052442  5/1982  European Pat. Off. .

*Primary Examiner*—John M. Ford
*Attorney, Agent, or Firm*—Sughrue, Mion, Zinn, Macpeak, and Seas

[57] ABSTRACT

A thiadiazine compound of the formula:

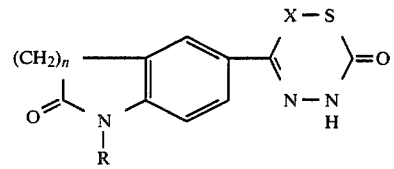

a method for preparing said compound and a pharmaceutical composition containing said compound, wherein X is methylene which may be optionally substituted by an alkyl of up to 3 carbon atoms; R is hydrogen atom or methyl group; and n is an integer of 1 or 2.

Since the compounds exhibit potent cardiotonic and coronary vasodilator activities and further inhibitory activity on platelet aggregation, they are useful as cardiotonic and antithrombotic drugs.

4 Claims, No Drawings

THIADIAZINE COMPOUNDS

FIELD OF THE INVENTION

This invention relates to novel and therapeutically valuable thiadiazine compounds, pharmaceutically acceptable acid addition salts thereof, method for preparing them and pharmaceutical compositions containing them. The compounds of this invention are useful for the treatment of acute or chronic heart failure.

BACKGROUND OF THE INVENTION

European patent application No. 0 052 442 discloses heterocyclic compounds of the formula:

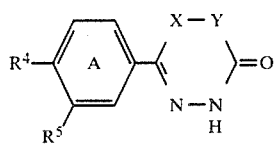

Wherein either X is —CR$^1$R$^2$— and Y is oxygen, sulphur or —NR$^3$—, wherein R$^1$, R$^2$ and R$^3$, which may be the same or different, each is hydrogen or alkyl of up to 4 carbon atoms; or X is oxygen, sulphur or —NH— and Y is —CH$_2$—; wherein R$^4$ and R$^5$, which may be the same or different, each is hydrogen, cyano, nitro, amino or hydroxy, or alkylthio of up to 4 carbon atoms, or has various other meanings defined in claim 1, provided that R$^4$ and R$^5$ are not both hydrogen; or wherein R$^4$ and R$^5$ are joined together such that with the benzene ring A they form a benzheterocyclic ring as defined in claim 1; and therein the benzene ring A may optionally bear one or more further substituents; or a salt thereof where appropriate.

These compounds possess cardiotonic properties, and some of them possess peripheral vasodilator properties.

On the other hand a compound of most interest under clinical investigation at present as a cardiotonic agent is 1,6-dihydro-2-methyl-6-oxo-[3,4'-bipyridine]-5-carbonitrile known by the name Milrinone, which has the structure:

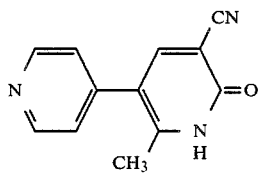

SUMMARY OF THE INVENTION

We have found that novel thiadiazine compounds, pharmaceutically acceptable acid addition salts thereof possess strong cardiotonic and coronary vasodilator properties, and further inhibitory properties on platelet aggregation. It is construed that the compounds are covered generally in the above EPA, but are not specifically disclosed. The compounds possess unexpected superior properties to the closest compound of the EPA. Further the compounds have advantages over milrinone.

DETAILED DESCRIPTION OF THE INVENTION

According to this invention there is provided a thiadiazine compound of the formula:

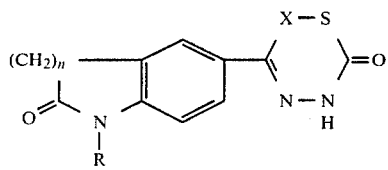

wherein X is methylene which may be optionally substituted by an alkyl of up to 3 carbon atoms; R is hydrogen atom or methyl group; and n is an integer of 1 or 2.

The compound can be prepared by reacting a compound of the formula:

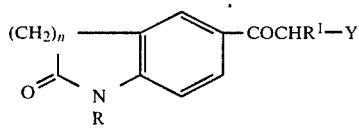

wherein R$^1$ is hydrogen atom or alkyl of up to 3 carbon atoms; and Y is a reactive atom or group such as halogen (e.g. chloride, bromide, of iodide) or alkanesulfonyloxy group (e.g. methylsulfonyloxy) or arenesulfonyloxy (e.g. benzenesulfonyloxy or p-toluenesulfonyloxy) with a compound of the formula:

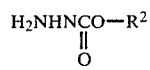

wherein R$^2$ is alkyl group, ammoniumion or alkaliion (e.g. sodium or potassium).

The reaction is carried out in a suitable solvent (e.g. methanol, ethanol, propanol, acetonitrile or dimethlyformamide) at from room temperature to the boiling point of a solvent used for from several to scores of hours.

The compounds of this invention can, if desired, be converted into pharmaceutically acceptable acid addition salts thereof in a conventional manner by treating with an inorganic acid (e.g. hydrochloric acid, hydrobromic acid, phosphoric acid, nitric acid or sulfuric acid) or an organic acid (e.g., p-toluene-sulfonic acid, methanesulfonic acid, citric acid, butyric acid, maleic acid, fumaric acid or tartaric acid).

The compounds and the pharmaceutically acceptable acid addition salts thereof exhibit potent cardiotonic and coronary vasodilator activities and further inhibitory activity on platelet aggregation as shown in the following pharmacological experiment, and are useful as cardiotonic and antithrombotic drugs.

1. Effects on max dp/dt and coronary blood flow by intracoronary administration in anesthetized dogs.

[Methods]

Dogs of either sex were anesthetized with sodium pentobarbital (30 mg/kg i.v.). Heparin (500 U/kg i.v.) was administered before making preparation. Under artificial respiration, left ventricular pressure and its first derivative (dp/dt), and left coronary blood flow were measured*. Test compounds were injected into the left coronary artery in a volume of 10 or 30 μl. The effects of compounds on coronary blood flow were presented as $ED_{50}$, a dose required to increase coronary blood flow by 50% of the effects of nifedipine (3 μg). Similarly, the effects on max dp/dt were shown as $ED_{30}$, a dose required to increase max dp/dt by 30% of the effects of isoproterenol (0.1 μg).

*Yago, N.: Folia pharmacol. Japon, 57, 380 (1961)

[Test compounds]
(1) 5-(3,4-dihydrocarbostyril-6-yl)-3,6-dihydro-1,3,4-thiadiazin-2-one
(2) 5-(5-oxindolyl)-3,6-dihydro-1,3,4-thiadiazin-2-one
(3) 5-(5-oxindolyl)-6-methyl-3,6-dihydro-1,3,4-thiadiazin-2-one
(4) 5-(1-methyl-3,4-dihydrocarbostyril-6-yl)-3,6-dihydro-1,3,4-thiadazin-2-one Comparison (A): 5-(1-acetylindolin-5-yl)-3,6-dihydro-1,3,4-thiadiazin-2-one disclosed in EPA 0052442

[Results]

| Compounds | Increase in max dp/dt $ED_{30}$ (μg) | Increase in CBF $ED_{50}$ (μg) |
|---|---|---|
| (1) | 1.5 | 30 |
| (2) | 4 | 30 |
| (3) | 10 | 15 |
| (4) | 10 | 5 |
| A | 50 | >300 |
| milrinone | 15 | 150 |

From these results, it is apparent that the cardiotonic effect of Compounds (1), (2), (3) and (4) are more potent than Comparison (A) and milrinone. In particular, (1) has the most potent effect, that is 33 times and 10 times more effective than (A) and milrinone, respectively. In addition, coronary vasodilating effect of (1) is over 10 times greater than (A) and 5 times greater than milrinone.

2. Effects of Platelet aggregation

[Methods]

Samples of blood were obtained from male rats. Platelet rich plasma (PRP) was prepared from blood by centrifuging at 200 g of 10 min. Platelet aggregation was measured at 37° C. with a turbidimetric device. The test solution or vehicle was added to PRP 2 min before the addition of ADP. Inhibition of platelet aggregation was assessed by comparing the area below the curve.

| Compounds | $IC_{50}$ (μg/ml) (in vitro) |
|---|---|
| (1) | 0.035 |
| (A) | 0.25 |
| Milrinone | 0.23 |

$IC_{50}$: Concentration required to inhibit platelet aggregation by 50%

[Results]

The inhibitory effect of Compound (1) on platelet aggregation was 7.1 times and 6.6 times more potent than Comparison (A) and milrinone, respectively.

In view of various tests including those mentioned above, the compounds of this invention, in base or salt form, can be safely administered as cardiotonic and antithrombotic drugs, in the form of a pharmaceutical preparation with a suitable and conventional pharmaceutically acceptable carrier, without adversely affecting the patients.

The pharmaceutical preparation can take any conventional form such as tablets, capsules, granules, powder or injectable solutions.

The following is an example of formulations when a compound of this invention is administered for pharmaceutical purposes:

Tablets (1 and 5 mg) are prepared from the following compositions:

| Compound | 1.0 mg | 5.0 mg |
|---|---|---|
| Lactose | 27.3 | 45.5 |
| Microcrystalline Cellulose | 20.0 | 30.0 |
| Corn Starch | 24.5 | 30.0 |
| Polyvinylpyrrolidone | 4.0 | 5.0 |
| Talc | 3.0 | 4.0 |
| Magnesium Stearate | 0.2 | 0.5 |
| | 80.0 mg | 120.0 mg |

The single dose of the compound of this invention for human adults usually ranges from about 1 mg/kg to about 5 mg/kg, but it may vary depending upon the age, body weight and/or severity of the conditions to be treated as well as the response to the medication.

EXAMPLE

To a solution of acetonitrile (100 ml) were added 6-chloroacetyl-3,4-dihydrocarbostyril (6.7 g) and ethoxythiocarbonylhydrazine (5.4 g) and the mixture was stirred for 2 hours, cooled and then filtered off. The filtrate was recrystallized from dimethylformamide (30 ml) and water (10 ml) to obtain pale yellowish 5-(3,4-dihydrocarbostyril-6-yl)-3,6-dihydro-1,3,4-thiadiazin-2-one (5.2 g), m.p. 271°–272° C. (decomposition).

The process described in the above was repeated using 5-chloroacetyloxindol, 5-(2-chloropropionyl)oxindol and 1-methyl-6-chloroacetyl-3,4-dihydrocarbostyril in place of 6-chloroacetyl-3,4-dihydrocarbostyril to obtain 5-(5-oxindolyl)-3,6-dihydro-1,3,4-thiadiazin-2-one m.p. above 310° C., 5-(5-oxindolyl)-6-methyl-3,6-dihydro-1,3,4-thiadiazin-2-one m.p. 265°–268° C. (decomposition) and 5-(1-methyl-3,4-dihydrocarbostyril-6-yl)-3,6-dihydro-1,3,4-thiadiazin-2-one m.p. 198° C.

What is claimed is:

1. 5-(3,4-dihydrocarbostyril-6-yl)-3,6-dihydro-1,3,4-thiadiazin-2-one.

2. A pharmaceutical composition comprising the compound of claim 1 in a therapeutically effective amount as a cardiotonic and a pharmaceutically acceptable carrier.

3. A pharmaceutical composition comprising the compound of claim 1 in a therapeutically effective amount as a coronary vasodilator and a pharmaceutically acceptable carrier.

4. A pharmaceutical composition comprising the compound of claim 1 in a therapeutically effective amount as an inhibitor in platelet aggregation and a pharmaceutically acceptable carrier.

* * * * *